United States Patent [19]

Budai et al.

[11] 4,395,413

[45] Jul. 26, 1983

[54] OXIME ETHERS AND PHARMACEUTICAL COMPOSITIONS CONTAINING THE SAME

[75] Inventors: Zoltán Budai; Aranka Lay née Kónya; Tibor Mezei; Lujza Petócz; Katalin Grasser; Ibolya Kosóczky; Enikó Szirt née Kiszelly; Péter Görög, all of Budapest, Hungary

[73] Assignee: Egyt Gyogyszervegyeszeti Gyar, Budapest, Hungary

[21] Appl. No.: 162,674

[22] Filed: Jun. 24, 1980

[30] Foreign Application Priority Data

Jul. 3, 1979 [HU] Hungary ............................ EE 2675

[51] Int. Cl.³ .................. A61K 31/15; C07D 295/08
[52] U.S. Cl. ................................ 424/250; 544/398; 544/165; 544/392; 548/569; 564/256; 564/257; 564/267
[58] Field of Search ............... 544/398; 564/267, 256, 564/257; 424/250, 316, 327

[56] References Cited

U.S. PATENT DOCUMENTS

1,733,462 10/1929 Krop .................................. 564/267
4,077,999 3/1978 Budai et al. ....................... 564/256

Primary Examiner—Anton H. Sutto
Attorney, Agent, or Firm—Young & Thompson

[57] ABSTRACT

The invention relates to novel oxime ethers of the general formula /I/ and acid addition salts and quaternary ammonium derivatives thereof,

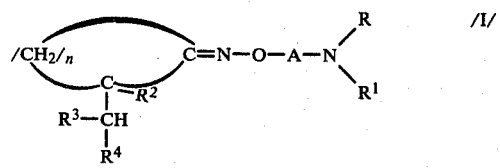

wherein
A represents a $C_{2-6}$ straight or branched alkylene chain,
R and $R^1$ each represent a $C_{1-6}$ alkyl group or they form together with the adjacent nitrogen atom a heterocyclic ring containing 4 to 7 carbon atoms and optionally a further hetero atom, i.e. an oxygen, sulfur or nitrogen atom, and said ring may be optionally substituted by a $C_{1-3}$ alkyl, phenyl or benzyl group,
$R^2$ and $R^3$ each denote a hydrogen atom or together form a valency bond,
$R^4$ denotes a $C_{1-10}$ alkyl or $C_{2-10}$ alkenyl group, and
n denotes an integer from 3 to 7.

The compounds of the general formula /I/ are prepared according to the invention by reacting a cycloalkane derivative of the general formula /II/

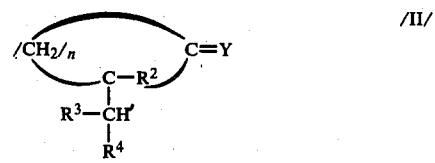

wherein
$R^2$, $R^3$, $R^4$ and n have the same meaning as above, whereas
Y denotes an oxygen or sulphur atom or a =N—OH group with an aminoalkyl derivative of the general formula /III/

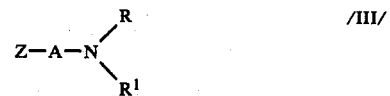

wherein
R, $R^1$ and A have the same meaning as stated above and
Z means a halogen atom or a $H_2N$—O— group or a salt thereof in the presence of a basic condensing agent.

The new compounds of the general formula /I/ possess valuable nicotine-lethality inhibiting, local anaesthetic, analgesic effects, which are, in case of certain compounds, complemented by anti-hypertensive, maximum electroshock and tetracorspasm inhibiting, ulcus inhibiting and motility inhibiting effects, and can be applied to advantage in the therapy.

7 Claims, No Drawings

OXIME ETHERS AND PHARMACEUTICAL COMPOSITIONS CONTAINING THE SAME

This invention relates to novel oxime ethers possessing valuable therapeutic effects and acid addition salts and quaternary ammonium derivatives thereof, furthermore to pharmaceutical compositions containing the same. The invention relates also to a process for their preparation.

It is known that certain basic 2-aryl-substituted cycloalkanone oxime ethers possess local anaesthetic and spasmolytic properties /published German patent application No. 26 09 017/.

According to a feature of the present invention there are provided compounds of the general formula /I/

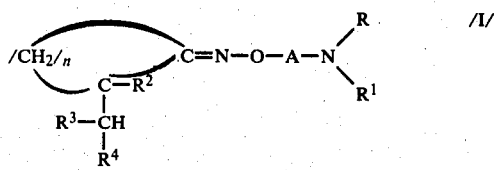

and pharmaceutically acceptable acid addition salts and quaternary ammonium derivatives thereof, wherein A represents a $C_{2-6}$ straight or branched alkylene chain, R and $R^1$ each represent a $C_{1-6}$ alkyl group or they form together with the adjacent nitrogen atom a heterocyclic ring containing 4 to 7 carbon atoms and optionally a further hetero atom, i.e. an oxygen, sulfur or nitrogen atom, and said ring may be optionally substituted by a $C_{1-3}$ alkyl, phenyl or benzyl group, $R^2$ and $R^3$ each denote a hydrogen atom or together form a valency bond, $R^4$ denotes a $C_{1-10}$ alkyl or $C_{2-10}$ alkenyl group, and n denotes an integer from 3 to 7.

The scope of the novel oxime ethers of the general formula /I/ comprises obviously also all their possible stereoisomers and the mixtures thereof.

Preferred representatives of the new compounds having the general formula /I/ are those wherein R and $R^1$ each represent methyl or ethyl group, or R and $R^1$ form, together with the adjacent nitrogen atom, an N-benzylpiperazinyl, N-methylpiperazinyl or piperazinyl ring, and $R^2$ and $R^3$ each denote hydrogen atom or together form a valency bond, and $R^4$ denotes ethyl, n-propyl, n-butyl, n-pentyl, n-heptyl or vinyl, A represents ethylene, propylene or isobutylene and n is 4, and the pharmaceutically acceptable acid addition salts of these compounds.

Of the new compounds of the general formula /I/ the following are particularly preferred:

2-n-butyl-1-/2'-dimethylaminoethoxyimino/-cyclohexane 2-n-butyl-1-/3'-dimethylaminopropoxyimino/-cyclohexane 2-n-butyl-1-/2'-methyl-3'-dimethylaminopropoxyimino/-cyclohexane 2-n-butyl-1-[3'-/4''-benzylpiperazinyl/-propoxyimino]-cyclohexane 2-n-butylidene-1-[3'-/4''-methylpiperazinyl/-propoxyimino]-cyclohexane 2-n-butylidene-[3'-/4''-benzylpiperazinyl/-propoxyimino]-cyclohexane 2-n-pentylidene-1-[3'-/4''-methylpiperazinyl/-propoxyimino]-cyclohexane 2-n-pentylidene-1-[3'-/4''-benzylpiperazinyl/-propoxyimino]-cyclohexane 2-allyl-[3'-/4''-methylpiperazinyl/-propoxyimino]-cyclohexane 2-n-hexylidene-1-[3'-/4''-methylpiperazinyl/-propoxyimino]-cyclohexane 2-n-octylidene-1-[3'-/4''-methylpiperazinyl/-propoxyimino]-cyclohexane and the pharmaceutically acceptable acid addition salts, particularly hydrochlorides, hydrogen fumarates, and fumarates thereof.

The term "alkyl" relates to straight-chained or branched saturated aliphatic hydrocarbyl groups, such as methyl, ethyl, n-propyl, isopropyl, n-butyl, etc. The term "alkenyl" refers to unsaturated hydrocarbyl groups, such as vinyl or allyl. The term "alkylene" relates to straight or branched chain aliphatic hydrocarbyl groups having two free valency bonds /e.g. ethylene, propylene, butylene, isobutylene, etc./. The heterocyclic ring formed by R, $R^1$ and the adjacent nitrogen atom may be pyrrolidine, piperidine, morpholine, piperazine, N-methyl-piperazine, N-phenyl-piperazine, N-benzyl-piperazine, etc.

According to a further feature of the present invention there is provided a process for the preparation of compounds of the general formula /I/ which comprises reacting a cycloalkane derivative of the general formula /II/

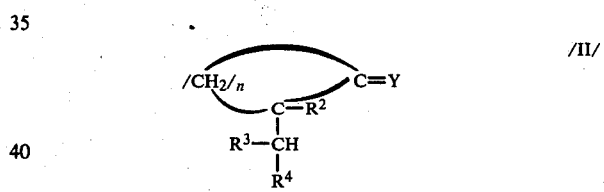

wherein $R^2$, $R^3$, $R^4$ and n have the same meaning as above, whereas

Y denotes an oxygen or sulfur atom or a =N—OH group with an aminoalkyl derivative of the general formula /III/

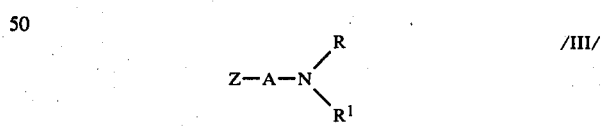

wherein

R, $R^1$ and A have the same meaning as stated above and

Z means a halogen atom or a $H_2N$—O— group or a salt thereof in the presence of a basic condensing agent.

The compounds of the general formula /II/ can be prepared by reacting a cycloalkanone with an aliphatic aldehyde or with an alkylhalide in a known way [Bull. Soc. Chim. Fr. 1967, 830–6, Rec. Trav. Chim. Pays-Bas 5, 481–503 /1967/; Helv. Chim. Acta 24, 209 /1964/].

Compounds of the general formula /III/, wherein Z represents a $H_2N$—O— group, can be prepared by the method described in J. Pharm. Sci. 58, 138–140 /1969/.

Compounds of the general formula /III/, wherein Z represents a halogen atom, are similarly known and commercially available.

The reaction of the compounds of the general formula /II/ and /III/ is preferably carried out in a solvent chemically inert toward the reactants, or in a mixture of such solvents. Inert solvents include, for example, alkanols /preferably ethanol/, pyridine, alkyl pyridines, triethylamine, benzene and its homologues, e.g. toluene, xylene, cresol, etc.; ethers, such as tetrahydrofurane, dibutylether, etc.; dimethyl formamide, dimethyl acetamide, or mixtures of any of these.

To assist the reaction of the compounds of the general formulae /II/ and /III/ a basic condensing agent is used. Depending on the nature of Y and Z an alkali metal, suitably sodium; an alkali metal amide, suitably sodium amide; an alkali metal hydroxide, suitably sodium hydroxide; or organic bases, e.g. pyridine, picoline, triethylamine, etc. may be used as condensing agents.

The reaction is carried out in a wide temperature range, e.g. from 25° C. to the boiling point of the solvent used, preferably at a temperature between 70° C. and 130° C.

The compounds of the general formula /I/ prepared according to the invention can be converted, if desired, into a therapeutically acceptable acid addition salt or a quaternary ammonium derivative in a known way. For the production of such addition salts e.g. hydrohalic acids, sulphuric acid, maleic acid, phosphoric acid, citric acid, tartaric acid, acetic acid, propionic acid, fumaric acid, maleic acid, methanesulphonic acid, etc. can be used. In order to produce quaternary ammonium compounds the compounds of the general formula /I/ are allowed to react with alkyl halides, dialkyl sulfates or methanesulphonic acid esters suitable for quaternisation. Thus the quaternary derivatives are preferably formed with $C_{1-6}$, preferably $C_{1-4}$ alkyl halides, dialkyl sulfates etc.

According to our investigations the compounds of the general formula /I/ proved to be biologically active in several tests. Of these biological effects the most significants were: the nicotine-lethality inhibiting effect, the local anaesthetic and the analgesic effect which are, in case of certain compounds, complemented by antihypertensive /hypotensive/, MES /maximum electroshock/ and tetracorspasm inhibiting, ulcus inhibiting and motility inhibiting effects.

The acut toxicity of the new compounds according to the invention was determined on white mice of both sexes weighing 18-24 g belonging to the strain CFLP. Administration was effected with an oral or intraperitoneal dosage of 20 ml/kg. After treatment the animals were kept under observation for 4 days. The toxicity data were determined by graphic method and are given in Table I.

TABLE I

| Compound | $LD_{50}$/mg/kg/ | |
|---|---|---|
| No. of Example | i.p. | per os. |
| 1 | 135 | 580 |
| 3 | 100 | 430 |
| 4 | 110 | 400 |
| 5 | 240 | 1300 |
| 7 | 330 | 1600 |
| 8 | 230 | 1450 |
| 9 | 200 | 3000 |
| 10 | 160 | 1800 |
| 14 | 310 | 1600 |

TABLE I-continued

| Compound | $LD_{50}$/mg/kg/ | |
|---|---|---|
| No. of Example | i.p. | per os. |
| 15 | 200 | 3000 |
| 16 | 270 | 3000 |

The inhibition of nicotine-lethality was determined on mice by the method of Stone /Stone, C. A. et al.: Arch. Intern. Pharmacodynamie 117, 419 /1958/. The results are given in Table II.

TABLE II

| Compound No. of Example | $ED_{50}$/p.o./ mg/kg | Therapeutic index |
|---|---|---|
| 7 | 155 | 10.0 |
| 15 | 190 | 16.0 |
| 16 | 150 | 17.6 |
| 14 | 70 | 22.0 |
| 9 | 150 | 20.0 |
| Trihexyphenidyl /Artane/ | 40 | 9.13 |

Therapeutic index = $\dfrac{LD_{50}}{ED_{50}}$

The local anaesthetic effect was investigated on the ischiadic nerve of rats by means of the method of Truant and d'Amato /Truant, A. P. and Wiedling, S.: Acta Chirurg. Scand. 116, 351 /1958//. Lidocaine served as reference substance. The number of animals exhibiting typical motor paralysis and the length of the duration of this effect were recorded.

In Table III. below, the relative efficiency referred to Lidocaine and the duration of the effect on application of 0.25% concentrations of Lidocaine are given.

TABLE III

| Compound No. of Example | $EC_{50}$ % conc. | Relative efficiency | Duration/minutes/ 0.25% |
|---|---|---|---|
| 4 | 0.15 | 1.13 | 31 |
| 9 | 0.25 | 0.76 | 64 |
| Lidocaine | 0.19 | 1.00 | 24 |

Relative efficiency = $\dfrac{EC_{50} \text{ Lidocaine}}{EC_{50} \text{ examined compound}}$ The analgesic effect was determined on mice by the method of Koster, R., Anderson, M., De Beer, E. J., Fred. Proc. 18, 412 /1959/. The results are summarized in Table IV.

TABLE IV

| Compound No. of Example | $ED_{50}$/p.o./ mg/kg | Therapeutic index |
|---|---|---|
| 1 | 320 | 5 |
| 8 | 290 | 5 |
| 9 | 500 | 6 |
| 5 | 250 | 5.2 |
| 3 | 45 | 9 |
| 10 | 140 | 13.0 |
| 16 | 200 | 15.0 |

The hypotensive effect of the new compounds was tested on anaesthesized cats. The compound of Example 7, administered in doses of 3 and 5 mg/kg, results in a prolonged decrease of blood pressure of 40 Hgmm. The compound also possesses a noradrenaline antagonistic /i.v. $ED_{50}$=2.3 mg/kg/ and isoproterenol antagonistic /i.v. $ED_{50}$=2.5 mg/kg/ effect. Beside its alpha- and beta-receptor blocking effect it decreases the effect on the carotid occlusion reflex. It has no influence on the orthostatic hypotension. This compound, orally tested on waking rats of normal tension in a dosage of 100 mg/kg, results in a decrease of blood pressure of 13 Hgmm.

The above data show that the compounds of the present invention surprisingly exhibit analgesic and hypotensive effects, too.

The compounds of the general formula /I/ and therapeutically acceptable acid addition salts or quaternary ammonium derivatives thereof may be formulated with the use of additives and/or carriers and/or adjuvants generally used in pharmacy, by standard techniques. Such compositions can be used mainly as antiparkinson, local anaesthetic and analgesic agents.

According to a further feature of the present invention there are provided the above pharmaceutical compositions which can be formulated in solid /e.g. tablets, capsules, coated pills, etc./ or liquid /e.g. solutions, suspensions, emulsions etc./ form. The carriers may be such generally used in pharmacy /e.g. starch, magnesium stearate, calcium carbonate, alginic acid, water, poliethylene glycole etc./. The compositions may also contain suitable additives /e.g. emulsifying, suspending, disintegrating agents, buffers, etc./.

A unitable dose of a pharmaceutical composition of the invention contains generally from 1 to 500 mg of a compound of the general formula /I/ or an acid addition salt or quaternary ammonium derivative thereof. Daily oral dose is about 1–100 mg/kg.

The invention is illustrated by the following Examples of non-limiting character.

EXAMPLE 1

Preparation of
2-n-butyl-1-/2'-dimethylaminoethoxyimino/-cyclohexane

The solution of 16.9 g /0.1 mole/ of 2-n-butylcyclohexanone oxime in 200 ml of anhydrous toluene is added, under continuous stirring, to a suspension of 2.4 g /0.1 mole/ of sodium hydride in 50 ml of anhydrous toluene, and the mixture is refluxed for 2 hours. Then 11.8 g /0.11 moles/ of 1-dimethylamino-2-chloroethane are added to the reaction mixture. After refluxing for 6 hours the mixture is cooled to room temperature, washed with water and extracted with a solution of 15 g /0.1 mole/ of tartaric acid in 100 ml of water /or with a solution of hydrochloric acid containing 0.11 moles of hydrochloric acid/. Then the solution is made alkaline to pH 10 with concentrated ammonium hydroxide. The base separated as an oil is extracted with dichloromethane. On distilling off the solvent, the residue is fractionated under vacuum.

Yield: 18.5 g /76.9%/ of a pale yellow oil
B.p.: 107°–108° C./53.32 Pa
Hydrogen fumarate, m.p.: 68°–69° C.
Analysis for $C_{18}H_{32}N_2O_5$: Calculated: C: 60.65%, H: 9.05%, N: 7.36%. Found: C: 60.17%, H: 9.44%, N: 7.40%.

EXAMPLE 2

Preparation of
2-n-butyl-1-/2'-diethylaminoethoxyimino/-cyclohexane

One proceeds according to Example 1, with the difference that, instead of 1-dimethylamino-2-chloroethane, 14.9 g /0.11 moles/ of 1-diethylamino-2-chloroethane are applied.

Yield: 19.3 g /72.1%/ of a pale yellow oil
B.p.: 114°–115° C./40.0 Pa
Hydrogen fumarate, m.p.: 73°–74.5° C.
Analysis for $C_{20}H_{36}N_2O_5$: Calculated: C: 62.47%, H: 9.43%, N: 7.28%. Found: C: 62.30%, H: 9.44%, N: 7.31%.

EXAMPLE 3

Preparation of
2-n-butyl-1-/3'-dimethylaminopropoxyimino/-cyclohexane

One proceeds in the way as specified in Example 1, with the difference that, instead of 1-dimethylamino-2-chloroethane, 13.3 g /0.11 moles/ of dimethylamino-3-chloropropane are applied.

Yield: 17.0 g /68.5%/ of a pale yellow oil
B.p.: 114°–115° C./40.0 Pa
Hydrogen fumarate, m.p.: 73°–75° C.
Analysis for $C_{19}H_{34}N_2O_5$: Calculated: C: 61.59%, H: 9.25%, N: 7.66%. Found: C: 61.70%, H: 9.40%, N: 7.52%.

EXAMPLE 4

Preparation of
2-n-butyl-1-/2'-methyl-3'-dimethylaminopropoxyimino/-cyclohexane

One proceeds in the way as specified in Example 1, with the difference that, instead of 1-dimethylamino-2-chloroethane, 16.5 g 0.11 moles/ of dimethylaminoisobutyl chloride are applied.

Yield: 18.7 g /69.8%/ of a pale yellow oil
B.p.: 115°–117° C./26.66 Pa
Hydrogen fumarate, m.p.: 120°–121° C.
Analysis for $C_{20}H_{35}N_2O_5$: Calculated: C: 62.47%, H: 9.43%, N: 7.28%. Found: C: 62.6%, H: 9.79%, N: 7.27%.

EXAMPLE 5

Preparation of
2-n-butyl-1-[3'-/4''-benzylpiperazinyl/-propoxyimino]-cyclohexane The solution of 16.9 g /0.1 mole/ of 2-n-butylcyclohexanoneoxime in 100 ml of anhydrous toluene is added dropwise to a suspension of 2.4 g /0.1 mole/ of sodium hydride in 100 ml of anhydrous toluene. The mixture is refluxed for 2 hours, then a solution of 27.8 g /0.11 moles/ of 1-/N-benzylpiperazinyl/-3-chloropropane in 50 ml of anhydrous toluene is added. After refluxing for 12 hours the reaction mixture is cooled and shaken with a solution of 35 g of tartaric acid in 150 ml of water. The aqueous phase is made alkaline to pH 10 with ammonium hydroxide. After extraction with dichloroethane, the solvent is removed and the residual base is processed to salt.

Yield: 27.5 g /71.6%/
Dihydrogen fumarate, m.p.: 200°–202° C.
Analysis for $C_{32}H_{42}N_3O_9$: Calculated: C: 62.72%, H: 6.90%, N: 6.89%. Found: C: 62.70%, H: 6.68%, N: 6.82%.

EXAMPLE 6

Preparation of
2-n-butyl-1-[3'-/4''-methylpiperazinyl/-propoxyimino]-cyclohexane One proceeds in the way as specified in Example 5, with the difference that, instead of 1-/N-benzylpiperazinyl/-3-chloropropane, 19.5 g /0.11 moles/ of 1-/N-methylpiperazinyl/-3-chloropropane are applied.

Yield: 28.0 g /92.4%/

Dihydrogen fumarate, m.p.: 199°–202° C.

Analysis for $C_{26}H_{43}N_3O_9$: Calculated: C: 57.64%, H: 8.00%, N: 7.75%. Found: C: 57.46%, H: 8.10%, N: 7.74%.

EXAMPLE 7

Preparation of
2-butylidene-1-[3'-/4''-methylpiperazinyl/-propoxyimino]-cyclohexane A sodium salt is prepared from 3.9 g /0.1 mole/ of sodium amide and 16.8 g /0.1 mole/ of 2-butylidenecyclohexanone oxime in a toluene medium, and then allowed to react with 19.5 g /0.11 moles/ of 1/-N-methylpiperazinyl/-3-chloropropane. Subsequently one proceeds in the way specified in Example 1.

Yield: 25.2 g /83.4%/

Dihydrogen fumarate, m.p.: 195°–197° C.

Analysis for $C_{26}H_{41}N_3O_9$: Calculated: C: 57.89%, H: 7.66%, N: 7.78%. Found: C: 57.65%, H: 7.52%, N: 7.70%.

Dihydrogen tartarate, m.p.: 72°–73° C.

Analysis for $C_{26}H_{45}N_3O$: Calculated: C: 51.39%, H: 7.46%, N: 6.92%. Found: C: 51.17%, H: 7.39%, N: 6.87%.

Dihydrochloride, m.p.: 184°–186° C.

Analysis for $C_{18}H_{35}Cl_2N_3O$: Calculated: C: 56.83%, H: 9.27%, Cl: 18.64%, N: 11.05%. Found: C: 56.68%, H: 9.11%, Cl: 18.60%, N: 11.00%.

1,1,4-Trimethyl-4[3'-/2''-butilidene-1''-cyclohexilidene/-oxypropyl]-piperazinodiiodide, m.p.: 269°–271° C.

Analysis for $C_{20}H_{39}N_3OI_2$: Calculated: C: 40.62%, H: 6.64%, N: 7.11%, I: 42.92%. Found: C: 41.01%, H: 6.82%, N: 7.10%, I: 43.10%.

EXAMPLE 8

Preparation of
2-butylidene-[3'-/4''-benzylpiperazinyl/-propoxyimino]-cyclohexane One starting from 2.4 g /0.1 mole/ of sodium hydride, 16.8 g /0.1 mole/ of 2-butylidenecyclohexanone oxime and 27.8 g /0.11 moles/ of 1-/N-benzylpiperazinyl/-3-chloropropane, one proceeds in the way as specified in Example 1.

Yield: 26.7 g /67.9%/

Dihydrogen fumarate, m.p.: 187°–189° C.

Analysis for $C_{32}H_{45}N_3O_9$: Calculated: C: 62.42%, H: 7.36%, N: 6.82%. Found: C: 62.30%, H: 7.50%, N: 6.78%.

EXAMPLE 9

Preparation of
2-pentylidene-1-[3'-/4''-methylpiperazinyl/-propoxyimino]-cyclohexane One starting from 2.4 g /0.1 mole/ of sodium hydride, 18.2 g /0.1 mole/ of 2-pentylidenecyclohexanone oxime and 19.5 g /0.11 moles/ of 1-/N-methylpiperazinyl/-3-chloropropane, one proceeds in the way specified in Example 5.

Yield: 25.8 g /79.5%/

Dihydrogen fumarate, m.p.: 193°–195° C.

Analysis for $C_{27}H_{43}N_3O_9$: Calculated: C: 58.49%, H: 7.82%, N: 7.59%. Found: C: 58.30%, H: 7.68%, N: 7.61%.

EXAMPLE 10

Preparation of
2-pentylidene-1-[3'-/4''-benzylpiperazinyl/-propoxyimino]-cyclohexane One proceeds in the way as specified in Example 5, with the difference that, instead of 2-butylcyclohexanone oxime 18.2 g /0.1 mole/ of 2-pentylidenecyclohexanone oxime are applied.

Yield: 25.3 g /63.6%/

Dihydrogen fumarate, m.p.: 200°–202° C.

Analysis for $C_{33}H_{47}N_3O_9$: Calculated: C: 62.93%, H: 7.52%, N: 6.67%. Found: C: 62.79%, H: 7.48%, N: 6.70%.

EXAMPLE 11

Preparation of
2-propylidene-1-[3'-/4''-methylpiperazinyl/-propoxyimino]-cyclohexane On starting from 2.4 g /0.1 mole/ of sodium hydride, 15.4 g /0.1 mole/ of 2-propylidenecyclohexanone oxime and 19.5 g /0.11 moles/ of 1-/N-methylpiperazinyl/-3-chloropropane, one proceeds in the way as specified in Example 5.

Yield: 24.2 g /82.5%/

Dihydrogen fumarate, m.p.: 188°–189° C.

Analysis for $C_{25}H_{39}N_3O$: Calculated: C: 57.14%, H: 7.48%, N: 7.95%. Found: C: 56.85%, H: 7.25%, N: 7.80%.

EXAMPLE 12

Preparation of
2-butylidene-1-[3'-/4''-methylpiperazinyl/-propoxyimino]-cycloheptane A sodium salt is formed from 2.4 g /0.1 mole/ of sodium hydride and 18.2 g /0.1 mole/ of 2-butylidenecycloheptanone oxime in a toluenic medium, then it is reacted with 19.5 g /0.11 moles/ of 1-/N-methylpiperazinyl/-3-chloropropane. Thereafter one proceeds as in Example 5.

Yield: 29.5 g /89.1%/

Dihydrogen fumarate, m.p.: 213°–216° C.

Analysis for $C_{27}H_{34}N_3O_9$: Calculated: C: 58.57%, H: 7.82%, N: 7.59%. Found: C: 58.25%, H: 7.56%, N: 7.38%.

EXAMPLE 13

Preparation of
2-butylidene-1-/2'-methyl-3'-dimethylaminopropoxyimino/-cyclohexane One proceeds in the way as specified in Example 1, with the difference that 16.8 g /0.1 mole/ of 2-butylidenecyclohexanone oxime and 16.5 g /0.11 moles/ of dimethylaminoisobutyl chloride are reacted.

Yield: 22.3 g /90.6%/

Hydrogen fumarate, m.p.: 134°–136° C.

Analysis for $C_{20}H_{34}N_2O_5$: Calculated: C: 62.68%, H: 8.95%, N: 7.32%. Found: C: 62.87%, H: 8.75%, N: 7.32%.

EXAMPLE 14

Preparation of
2-allyl-[3'-/4''-methylpiperazinyl/-propoxyimino]-cyclohexane

A sodium salt is formed from 2.4 g /0.1 mole/ of sodium hydride and 15.3 g /0.1 mole/ of 2-allylcyclohexanone oxime, then it is reacted with 19.5 g /0.11 moles/ of 1-/N-methylpiperazinyl/-3-chloropropane. Thereafter one proceeds as in Example 5.

Yield: 25.2 g /86.1%/
Dihydrogen fumarate, m.p.: 192°–195° C.
Analysis for $C_{25}H_{38}N_3O$: Calculated: C: 57.24%, H: 7.30%, N: 8.01%. Found: C: 57.00%, H: 7.45%, N: 8.02%.

EXAMPLE 15

Preparation of 2-hexylidene-1-[3'-/4''-methylpiperazinyl/propoxyimino]-cyclohexane On starting from 2.4 g /0.1 mole/ of sodium hydride, 19.5 g /0.1 mole/ of 2-hexylidenecyclohexanone oxime and 19.5 g /0.11 moles/ of 1-/N-methylpiperazinyl/-3-chloropropane, one proceeds in the way as specified in Example 5.

Yield: 28.8 g /86.1%/
Analysis for $C_{28}H_{45}N_3O_9$: Calculated: C: 59.24%, H: 7.99%, N: 7.40%. Found: C: 59.01%, H: 8.02%, N: 7.36%.

EXAMPLE 16

Preparation of 2-octylidene-1-[3'-/4''-methylpiperazinyl/propoxyimino]-cyclohexane One starts from 2.4 g /0.1 mole/ of sodium hydride and 22.3 g /0.1 mole/ of 2-octylidenecyclohexanone oxime, thereafter the sodium salt formed in a toluene medium is reacted with 19.5 g /0.11 moles/ of 1-/N-methylpiperazinyl/-3-chloropropane in the way as specified in Example 5.

Yield: 30.5 g /84.0%/
Dihydrogen fumarate, m.p.: 200°–203° C.
Analysis for $C_{30}H_{49}N_3O_9$: Calculated: C: 60.48%, H: 8.29%, N: 7.05%. Found: C: 60.62%, H: 8.36%, N: 1.10%.

EXAMPLE 17

Preparation of 2-n-butyl-1-/2'-diethylaminoethoxyimino/-cyclohexane 15.4 g /0.1 mole/ of 2-n-butylcyclohexanone and 22.61 g /0.11 moles/ of diethylaminoethoxyamine dihydrochloride are boiled for a few hours in a mixture of 15 ml of anhydrous ethanol and 74 ml of anhydrous pyridine, then the mixture is evaporated under vacuum. The residue is made alkaline with a 40% aquous solution of sodium hydroxide, the base is extracted with dichloroethyne, then the solvent is removed.

Yield: 21.23 g /79.3%/ of a pale yellow oil.
B.p.: 114°–115° C./40.0 Pa
Hydrogen fumarate, m.p.: 73°–74° C.
Analysis for $C_{20}H_{36}N_2O_5$: Calculated: C: 62.47%, H: 9.43%, N: 7.28%. Found: C: 62.30%, H: 9.44%, N: 7.31%.

EXAMPLE 18

Preparation of 2-n-butyl-1-/2'-dimethylaminoethoxyimino/-cyclohexane

On starting from 15.4 g /0.1 mole/ of 2-n-butylcyclohexanone and 17.7 g /0.11 moles/ of dimethylaminoethoxyamine dihydrochloride one proceeds in the way as specified in Example 17.

Yield: 20.4 g /84.6%/
Hydrogen fumarate, m.p.: 68°–69° C.

EXAMPLE 19

Preparation of 2-n-butyl-1-/2'-methyl-3'-dimethylaminopropoxyimino/-cyclohexane

On starting from 15.4 g /0.1 mole/ of 2-n-butylcyclohexanone and 30.76 g /0.15 moles/ of dimethylaminoisobutyl amine dihydrochloride, one proceeds in the way as described in Example 17.

Yield: 20.60 g /76.8%/
Hydrogen fumarate, m.p.: 120°–121° C.

EXAMPLE 20

Preparation of 2-n-butyl-1-/3'-dimethylaminopropoxyimino/-cyclohexane

On starting from 15.4 g /0.1 mole/ of 2-n-butylcyclohexanone and 21.0 g /0.11 moles/ of dimethylaminopropoxyamine dihydrochloride, one proceeds in the way as specified in Example 17.

Yield: 20.0 g /78.8%/
Hydrogen fumarate, m.p.: 73°–75° C.

EXAMPLE 21

Preparation of 2-butyl-1-[3'-/4''-benzylpiperazinyl]-propoxyimino]-cyclohexane

On starting from 15.4 g /0.1 mole/ of 2-n-butylcyclohexanone and 37.7 g /0.11 moles/ of 1-/aminooxypropyl/-4-benzyl-piperazine trihydrochloride, one proceeds in the way specified in Example 17.

Yield: 28.9 g /75.6%/
Dihydrogen fumarate, m.p.: 201°–202° C.

EXAMPLE 22

Preparation of 2-n-butyl-1-[3'-4''-methylpiperazinyl-propoxyimino]-cyclohexane

On starting from 15.4 g /0.1 mole/ of 2-n-butylcyclohexanone and 31.1 g /0.11 moles/ of 1-aminooxypropyl-4-methylpiperazine trihydrochloride, one proceeds in the way as specified in Example 17.

Yield: 28.9 g /95.4%/
Dihydrogen fumarate, m.p.: 211°–213° C.

EXAMPLE 23

Preparation of 2-butylidene-1-[3'-4''-benzylpiperazinyl-propoxyimino]-cyclohexane On starting from 15.2 g /0.1 mole/ of 2-butylidenecyclohexanone and 37.7 g /0.11 moles/ of 1-/aminooxypropyl/-4-benzylpiperazine trihydrochloride, one proceeds in the way as specified in Example 17.

Yield: 30.62 g /77.9%/
Dihydrogen fumarate, m.p.: 187°–189° C.

EXAMPLE 24

Preparation of 2-pentylidene-1-[3'-4''-benzylpiperazinylpropoxyimino]-cyclohexane On starting from 16.6 g /0.1 mole/ of 2-pentylidenecyclohexanone and 37.7 g /0.1 mole/ of 1-/aminoxypropyl/-4-benzylpiperazinyl trihydrochloride, one proceeds in the way as specified in Example 17.

Yield: 27.83 g /70%/
Dihydrogen fumarate, m.p.: 200°–202° C.

EXAMPLE 25

Preparation of
2-allyl-1-[3'-/4"-methylpiperazinyl/-propoxyimino]-cyclohexane

On starting from 13.8 g /0.1 mole/ of 2-allylcyclohexanone and 31.1 g /0.11 moles/ of 1-/aminooxypropyl/-4-methylpiperazine trihydrochloride, one proceeds in the way as specified in Example 17.

Yield: 22.68 g /77.5%/
Dihydrogen fumarate, m.p.: 194°–196° C.

EXAMPLE 26

Preparation of
2-butylidene-1-[3'-/4"-methylpiperazinyl/-propoxyimino]-cyclohexane On starting from 15.2 g /0.11 moles/ of 2-butylidenecyclohexanone and 31.1 g /0.11 moles/ of 1-/aminooxypropyl/-4-methylpiperazine trihydrochloride, one proceeds in the way as specified in Example 17.

Yield: 27.7 g /91.7%/
Dihydrogen fumarate, m.p.: 197°–198° C.

EXAMPLE 27

Preparation of
2-butylidene-1-[3'-/4"-methylpiperazinyl/-propoxyimino]-cycloheptane On starting from 16.6 g /0.1 mole/ of 2-butylidenecycloheptanone and 31.1 g /0.11 moles/ of 1-/aminooxypropyl/-4-methylpiperazine trihydrochloride, one proceeds in the way as specified in Example 17.

Yield: 28 g /84.5%/
Dihydrogen fumarate, m.p.: 215°–217° C.

EXAMPLE 28

Preparation of
2-pentylidene-1-[3'-/4"-methylpiperazinyl/-propoxyimino]-cyclohexane On starting from 16.6 g /0.1 mole/ of 2-pentylidenecyclohexanone and 31.1 /0.11 moles/ of 1-/aminooxypropyl/-4-methylpiperazine trihydrochloride, one proceeds in the way as described in Example 17.

Yield: 28.4 g /87.5%/
Dihydrogen fumarate, m.p.: 194°–196° C.

EXAMPLE 29

Preparation of
2-propylidene-1-[3'-/4"-methylpiperazinyl/-propoxyimino]-cyclohexane On starting from 13.8 g /0.1 mole/ of 2-propylidenecyclohexanone and 31.1 g /0.11 moles/ of 1-/aminooxypropyl/-4-methylpiperazine trihydrochloride, one proceeds in the way as specified in Example 17.

Yield: 22.99 g /78.4%/
Dihydrogen fumarate, m.p.: 189°–190° C.

EXAMPLE 30

Preparation of
2-butylidene-1-[3'-/4"-methylpiperazinyl/-propoxyimino]-cyclohexane On starting from 16.8 g /0.1 mole/ of 2-butylidenecyclohexathion and 31.1 g /0.11 moles/ of 1-/aminooxypropyl/-4-methylpiperazine trihydrochloride, one proceeds in the way as described in Example 17.

Yield: 21 g /70.3%/

EXAMPLE 31

Preparation of
2-butylidene-1-[3'-/4"-methylpiperazinyl/-propoxyimino]-cyclohexane A sodium methylate solution is prepared from 6.9 g /0.3 g-atoms/ of sodium metal and 50 ml of anhydrous methanol, and then a solution of 16.8 g /0.1 mole/ of 2-butylidenecyclohexanone oxime in 150 ml of anhydrous methanol is added to it. After the evolution of hydrogen gas has ceased 27.5 g /0.11 moles/ of 1-/N-methylpiperazinyl/-3-chloropropane dihydrochloride are cautiously added to the reaction mixture. After refluxing for a few hours the salt is removed and the resulting mixture is evaporated.

Yield: 29.5 g /97.6%/
Dihydrogen fumarate, m.p.: 196°–198° C.

EXAMPLE 32

Preparation of
2-butylidene-1-[3'-/4"-methylpiperazinyl/-propoxyimino]-cyclohexane A solution of 16.8 g /0.1 mole/ of 2-butylidenecyclohexanone oxime in 150 ml of anhydrous toluene is added to a suspension of 4.4 g /0.1 mole/ of sodium hydride in 50 ml of anhydrous toluene and 30 ml of anhydrous dimethylformamide. The mixture is kept for two hours at 100° C., then 19.5 g /0.11 moles/ of 1-/N-methylpiperazinyl/-3-chloropropane are added and the mixture is kept for a few hours at 100° C. Thereafter the reaction mixture is washed twice with 50 ml of water and evaporated in vacuum.

Yield: 26.2 g /86.7 %/
Dihydrogen fumarate, m.p.: 196°–197° C.

EXAMPLE 33

Preparation of
2-allyl-1-[3'-/4"-methylpiperazinyl/-propoxyimino]-cyclohexane 2.4 g /0.1 mole/ of sodium hydride is reacted with 15.3 g /0.1 mole/ of 2-allylcyclohexanone oxime and with 19.5 g /0.11 moles/ of 1-/N-methylpiperazinyl-3-chloropropane in the way as described in Example 32 with the difference that 30 ml of dimethylacetamide are applied instead of dimethylformamide.

Yield: 26.2 g /88.4 %/
Dihydrogen fumarate, m.p.: 194°–196° C.

EXAMPLE 34

Preparation of
2-butylidene-1-/2'-methyl-3'-dimethylamino-propoxyimino/-cyclohexane One proceeds in the way as specified in Example 17, with the difference that 15.2 g /0.1 mole/ of 2-butylidenecyclohexanone and 22.6 g /0.11 moles/ of 1-dimethylamino-2-methyl-2-aminooxypropane dihydrochloride are applied.

Yield: 22.9 g /93 %/

Hydrogen fumarate, m.p.: 134°–136° C.

EXAMPLE 35

Tablets containing 25 mg of 2-butyl-1-/2′-dimethylaminoethoxyimino/-cyclohexane hydrogen fumarate are prepared The composition of a tablet is as follows:

| Active ingredient | 25.0 mg |
|---|---|
| Maize starch | 97.0 mg |
| Polyvinyl pyrrolidone | 175.0 mg |
| Magnesium stearate | 3.0 mg |
| | 300.0 mg |

After moistening with a 10–15% aqueous solution of polyvinyl pyrrolidone, a mixture of the active ingredient and the maize starch is granulated and subsequently dried at 40°–45° C. After repeated drying the granulate is mixed with the magnesium stearate and pressed into tablets weighing 300 mg.

EXAMPLE 36

Dragées containing 25 mg of 2-butylidene-1-[3′-/4″-methylpiperazinyl/-propoxyimino]-cyclohexane dihydrogen fumarate are prepared The composition of a dragée kernel is as follows:

| Active ingredient | 25.0 mg |
|---|---|
| Maize starch | 245.0 mg |
| Gelatine | 8.0 mg |
| Talk | 18.0 mg |
| Magnesium stearate | 4.0 mg |
| | 300.0 mg |

A mixture of the active ingredient and the maize starch is moistened with a 10% aqueous gelatine solution, then granulated by passing through a sieve and dried at 40°–45° C. The dry granulate is repeatedly sieved, homogenized with the talc and the magnesium stearate, finally compressed to dragée kernels of 300 mg each.

EXAMPLE 37

Dragées containing 50 mg of 2-octylidene-1-[3′-/4″-methylpiperazinyl/-propoxyimino]-cyclohexane dihydrogen fumarate are prepared The composition of a dragée kernel is as follows:

| Active ingredient | 50.0 mg |
|---|---|
| Lactose | 97.0 mg |
| Polyvinyl pyrrolidone | 2.0 mg |
| Magnesium stearate | 1.0 mg |
| | 150.0 mg |

The granulate is prepared as in the foregoing Example. The weight of a dragée kernel is equal to 150 mg. The dragée kernels are coated in a manner known per se, by a layer consisting of sugar and talc. The finished dragée is coloured with a suitable non-toxic food pigment and polished with beewax.

EXAMPLE 38

Gelatine capsules containing 25 mg of active ingredient are prepared

The composition of a gelatine capsule is as follows:

| Active ingredient | 25.0 mg |
|---|---|
| Maize starch | 265.0 mg |
| Aerosil | 6.0 mg |
| Magnesium stearate | 4.0 mg |
| | 300.0 mg |

The components are homogenized and then filled into gelatine capsules of an adequate size.

EXAMPLE 39

Gelatine capsules containing 50 mg of active ingredient are prepared

| Active ingredient | 50.0 mg |
|---|---|
| Lactose | 90.0 mg |
| Aerosil | 6.0 mg |
| Magnesium stearate | 4.0 mg |
| | 150.0 mg |

The components are homogenized and then filled into gelatine capsules of an adequate size.

EXAMPLE 40

An injectable solution containing 25 mg of active substances is prepared

An ampoule contains 25.0 mg of the active ingredient in 5 ml of twice distilled water.

What we claim is:

1. An oxime ether of the general formula /I/ or a pharmaceutically acceptable acid addition salt thereof,

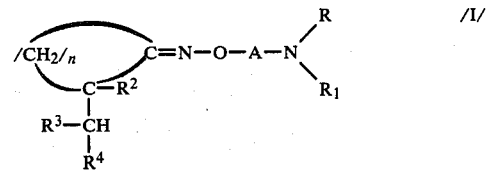

wherein

A represents a $C_{2-6}$ straight or branched alkylene chain,

R and $R^1$ each represent a $C_{1-6}$ alkyl group or they form together with the adjacent nitrogen atom a piperazinyl group optionally substituted with a $C_{1-3}$ alkyl or benzyl group, $R^2$ and $R^3$ each denote a hydrogen atom or together form a valency bond, $R^4$ denotes a $C_{1-10}$ alkyl or $C_{2-10}$ alkenyl group, and n is 4 or 5.

2. A compound as claimed in claim 1, wherein $R^4$ denotes ethyl, n-propyl, n-butyl, n-pentyl, n-heptyl or vinyl group.

3. A compound as claimed in claim 1 or 2, wherein A represents ethylene, propylene or isobutylene group.

4. A compound as claimed in claim 1, wherein R and $R^1$ each represent methyl or ethyl group, or they form, together with the adjacent nitrogen atom, an N-benzylpiperazinyl, N-methylpiperazinyl or piperazinyl ring.

5. A compound as claimed in claim 1, wherein n is 4.

6. 2-n-Butyl-1-/2'-dimethylaminoethoxyimino/-cyclohexane, 2-n-butyl-1-/3'-dimethylaminopropoxyimino/-cyclohexane, 2-n-butyl-1-/2'-methyl-3'-dimethylaminopropoxyimino/-cyclohexane, 2-n-butyl-1-[3'-/4''-benzylpiperazinyl/-propoxyimino]-cyclohexane, 2-n-butylidene-1-[3'-/4''-methylpiperazinyl/-propoxyimino]-cyclohexane, 2-n-butylidene-[3'-/4''-benzylpiperazinyl/-propoxyimino]-cyclohexane, 2-n-pentylidene-1-[3'-/4''-methylpiperazinyl/-propoxyimino]-cyclohexane, 2-n-pentylidene-1-[3'-/4''-benzylpiperazinyl/-propoxyimino]-cyclohexane, 2-allyl-[3'-/4'''-methylpiperazinyl/-propoxyimino]-cyclohexane, 2-n-hexylidene-1-[3'-/4''-methylpiperazinyl/-propoxyimino]-cyclohexane, 2-n-octylidene-1-[3'-/4''-methylpiperazinyl/-propoxyimino]-cyclohexane, or a pharmaceutically acceptable acid addition salt thereof.

7. A nicotine lethality-inhibiting pharmaceutical composition containing as active ingredient a nicotine lethality-inhibiting effective amount of a compound as claimed in claim 1, together with a pharmaceutical excipient.

* * * * *